United States Patent [19]

Oquendo et al.

[11] Patent Number: 4,872,992

[45] Date of Patent: Oct. 10, 1989

[54] METHOD AND APPARATUS FOR ANALYZING DILUTED AND UNDILUTED FLUID SAMPLES

[75] Inventors: Javier N. Oquendo, Denton; Joseph A. Leone, Plano, both of Tex.

[73] Assignee: Atlantic Richfield Company, Los Angeles, Calif.

[21] Appl. No.: 130,831

[22] Filed: Dec. 9, 1987

[51] Int. Cl.⁴ ............................................. B01D 15/08
[52] U.S. Cl. ................................. 210/659; 210/198.2; 422/70; 422/81; 436/52; 436/150; 436/161
[58] Field of Search ................... 436/52, 150, 161; 422/70, 81; 210/635, 656, 659, 198.2

[56] References Cited

U.S. PATENT DOCUMENTS

| | | | |
|---|---|---|---|
| 3,373,872 | 3/1968 | Hrdina | 422/70 |
| 3,375,080 | 3/1968 | Fujii | 422/70 |
| 3,847,550 | 11/1974 | Scott | 422/70 |
| 3,923,460 | 12/1975 | Parrott | 422/70 |
| 3,926,559 | 12/1975 | Stevens | 436/161 |
| 4,070,284 | 1/1978 | Fujita | 436/161 |
| 4,112,743 | 9/1978 | Mowery | 422/70 |
| 4,165,219 | 8/1979 | Huber | 422/70 |
| 4,274,967 | 6/1981 | Snyder | 436/161 |
| 4,290,776 | 9/1981 | Yamada | 436/161 |
| 4,387,075 | 6/1983 | Morgart | 422/70 |
| 4,419,452 | 12/1983 | Imai | 436/161 |
| 4,715,216 | 12/1987 | Muller | 422/70 |

Primary Examiner—Ernest G. Therkorn
Attorney, Agent, or Firm—Michael E. Martin

[57] ABSTRACT

Ion chromatograms are prepared with a chromatograph including a separation column and a conductivity measuring ion detection unit which are adapted to be selectively placed in communication with separate reservoirs for diluted and undiluted samples of a fluid to be analyzed. A control unit switches the reservoirs into communication with an eluent pump for displacing fluid samples through the detection unit in timed relationship such that the most concentrated ion is measured in the diluted sample prior to measurement by the detection unit of the last of the lesser concentrated ions. A pump having a controllable flow rate is connected to a mixing conduit through control valves which switch the flow to and from the reservoirs so that the reservoirs may be simultaneously filled with diluted and undiluted samples of fluid. The diluted sample may be prepared by mixing the undiluted fluid with the eluent.

5 Claims, 2 Drawing Sheets

METHOD AND APPARATUS FOR ANALYZING DILUTED AND UNDILUTED FLUID SAMPLES

BACKGROUND OF THE INVENTION

1. Field of the Invention

The present invention pertains to an improved method of analyzing fluids and an apparatus, such as an ion chromatograph, in which fluid samples are automatically injected into a detection unit in both diluted and undiluted conditions for simultaneous determination of the concentration of major and minor components of the fluid.

2. Background

Laboratory analysis of fluid samples in large numbers is carried out routinely. For example, in the petroleum exploration and production industry the analysis of various brines obtained from sea water, ground water and process samples are carried out with ion chromatographs and other spectrographic devices. The wide range of concentrations of the ionized components often requires dilution of the fluid samples to make possible the measurement of high concentrations of certain ions which, if the sample is not diluted, are present at concentrations beyond the measurement range of the detector. In some instances, if a fluid sample is not diluted before analysis, the major components cannot be quantified because they are present in concentrations beyond the linear response region of the detector device, the purity of recorded peaks or maximum concentrations having large elution volumes is questioned due to the tendency of adjacent peaks on the chromatogram to overlap as the concentration of one or both components increase, or retention times cannot be used for identification purposes because of abnormal readings and certain ion migration phenomena.

Conversely, if the fluid sample is diluted to lower the concentration of the so-called major ion components, one or more of the minor components to be measured cannot be reliably determined because their concentrations become close to or less than the limit of detection. As a result, a two step analysis is required which can be very time consuming and expensive when large numbers of samples are required to be measured. Accordingly, the present invention is directed to improvements in ion chromatograph methods and systems for measuring the ion concentrations in fluid samples, which improvements eliminate the need to prepare and inject into the chromatograph detection unit different standard solutions or prepare and handle a particular fluid sample twice, namely, in both diluted and undiluted concentrations.

The desired results of the present invention include obtaining the concentrations of all of the components of a fluid sample in a single graphic or numerical display such that a single chromatogram will show the concentrations of all components. Accordingly, significant savings in time for analyzing a particular type of fluid is realized by the improved method and apparatus of the invention.

SUMMARY OF THE INVENTION

The present invention pertains to an improved apparatus and method for analyzing the composition of a fluid sample wherein diluted and undiluted samples may be automatically prepared and essentially simultaneously analyzed.

In accordance with one aspect of the present invention, an improved ion chromatograph is provided wherein a fluid sample of a particular concentration may be passed through a separation column and an ion detection unit and a diluted sample of the same fluid may also be automatically prepared and injected through the separation column and detection unit whereby the concentrations of the various ion components of the fluid may be measured and recorded substantially simultaneously.

In accordance with yet another aspect of the present invention, there is provided a method and an improved apparatus for preparing a diluted sample of a fluid composition to be analyzed wherein the sample dilution may be automatically controlled. Moreover, depending on the fluid sample being measured, the eluent and diluent may comprise the same fluid in instances, for example, in analyzing various brine solutions.

Still further, the present invention provides an improved ion chromatograph wherein an arrangement of fluid conducting control valves is configured to prepare and inject samples of fluid to an ion separation column and an ion detection unit whereby the composition of a fluid sample in both a diluted condition or an undiluted condition may be recorded. The improved configuration of the chromatograph may be utilized in a conventional operating mode and in the improved operating mode.

The present invention permits the simultaneous determination of major and minor components of a fluid within a chromatograph operation time that is less than the sum of the operating times required of prior art operating modes. The improved operating mode not only saves time but requires less computer data storage or memory capacity, does not require any substantial new hardware or software, particularly when considering a particular type of commercially available chromatograph, results in savings in the use of chemical reagents, when compared to other dilution schemes, provides for switching between selected modes of operation, can be used to preconcentrate very dilute fluid samples and has a wide range of applications. These and other advantages and desirable aspects of the present invention will be further appreciated by those skilled in the art upon reading the detailed description which follows in conjunction with the drawing.

DESCRIPTION OF PREFERRED EMBODIMENTS

Figure 1:
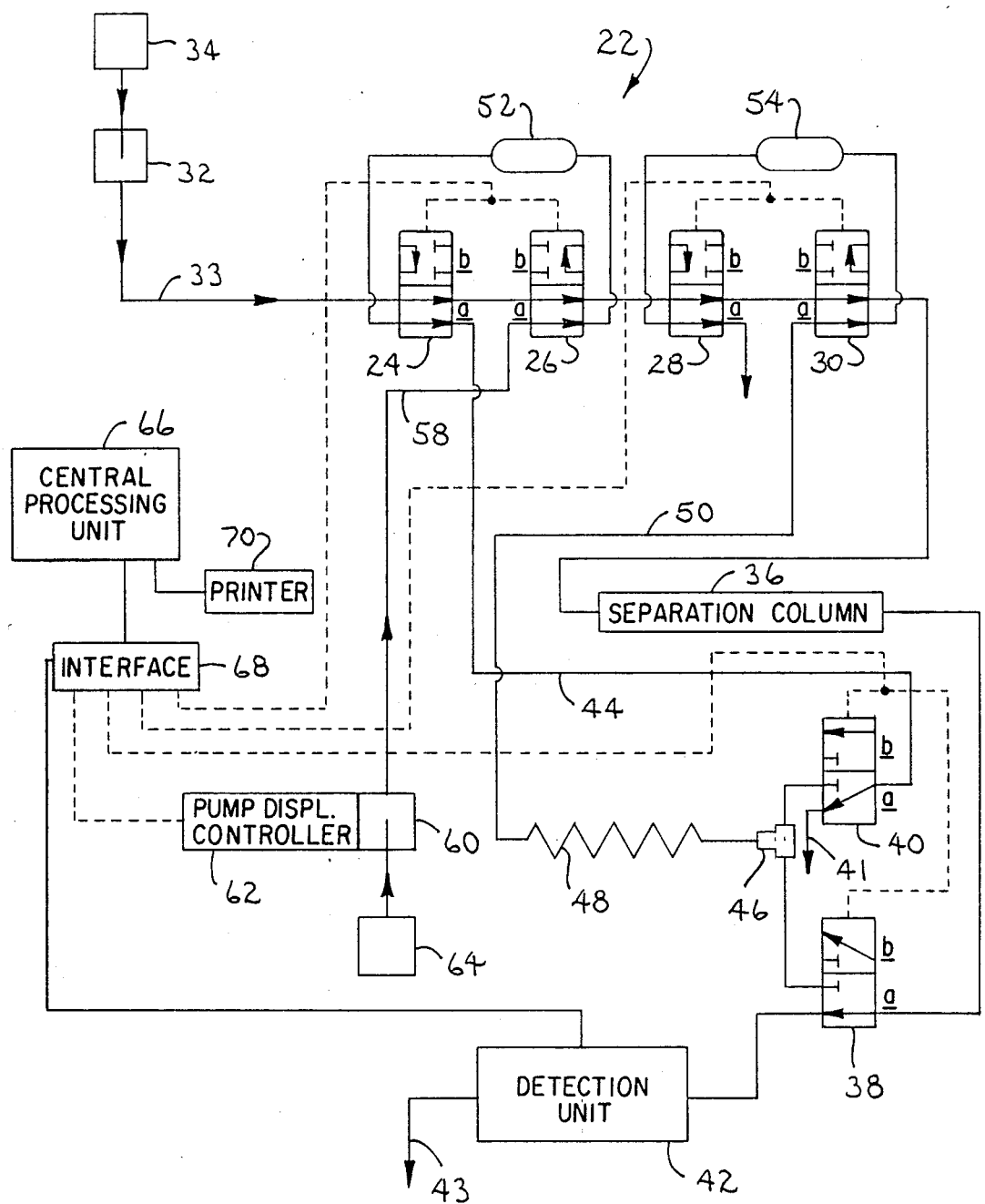
FIG. 1 is a schematic diagram of the improved fluid analysis apparatus or system of the present invention.

In the description which follows and in the drawing conventional elements are described in general terms and are shown in somewhat schematic form in the interest of clarity and conciseness.

Figure 2:
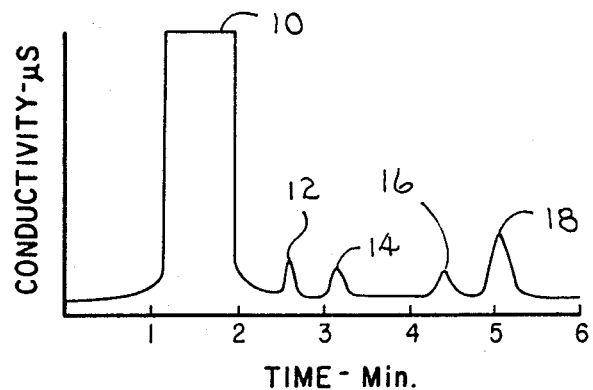
FIGS. 2 through 4 are diagrams illustrating the measurement of ion concentrations in a fluid sample in selected modes of operation in accordance with the improved apparatus and method of the present invention.
Figure 3:
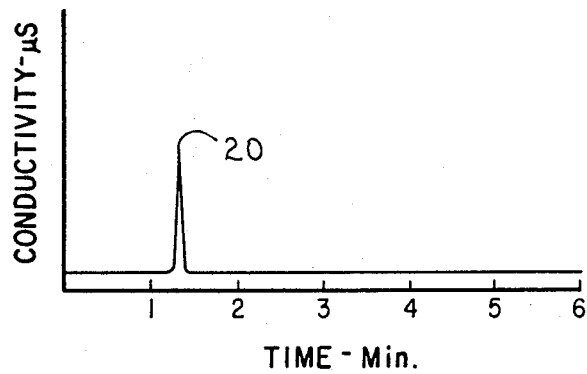
Figure 4:
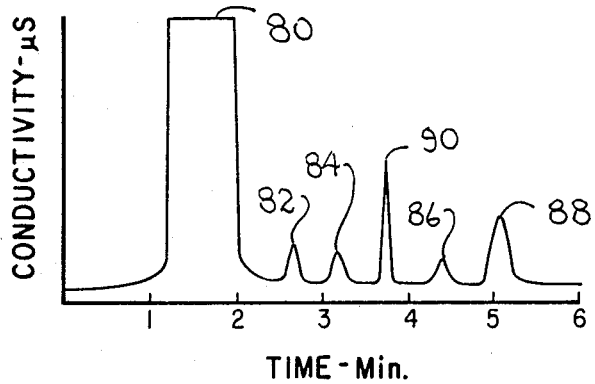

In the analysis of brine solutions, for example, commercial ion chromatographs often require that a two step analysis be carried out to measure the presence of ions of high concentration as well as those ions of lesser concentrations. For example, FIG. 2 represents a plot of the conductivity of various ions detected in a brine solution versus time when the solution is passed through an ion concentration column and a conductivity measuring type ion detection unit. In FIGS. 2 through 4 the scale of the ordinate is indicated in micro siemens and the abscissa is time in minutes. In FIG. 2, the concentration of the most highly concentrated ion is indicated by the peak 10 and is so great that the apparatus is not able to measure the concentration and the response of the detector is no longer linear. The concentrations of lesser concentrated ions are, however, measurable as indicated by the peaks 12, 14, 16 and 18. On the other hand, as shown in FIG. 3 a diluted sample of fluid passed through the separation column and the detection unit may only be capable of detection of the most concentrated ion, as indicated by the peak 20, while the lesser concentrated ions have been so diluted that they are not measurable by the conductivity measuring type detection unit. Not only are two samples required to be independently prepared, loaded and injected into the apparatus, but the data output of the apparatus normally appears on two separate record or displays. The present invention overcomes the problems associated with measuring the compositions of fluids having relatively high concentrations of particular components and relatively low concentrations of other components as will be appreciated by the further description herein.

FIG. 1 illustrates a somewhat simplified schematic diagram of a modified, commercially available ion chromatograph such as a Model 2120 Ion Chromatograph manufactured by Dionex Corporation, Sunnyvale, Calif. The apparatus illustrated in FIG. 1 is generally designated by the numeral 22 and includes power operated valves 24 and 26 which are adapted to be shifted simultaneously between their positions a and positions b to in effect operate as one valve unit. The apparatus 22 further includes power operated valves 28 and 30 which are also adapted to operate as one valve simultaneously between their respective positions a and b.

The valve 24 is adapted to be in communication with a pump 32 for supplying on a substantially continuous basis an eluent from a source 34. The eluent may be a suitably deionized water treated with salts and acids of a type commercially available and appropriate for the particular analysis to be carried out. The valve 30 is in communication with an ion separation column 36 comprising part of the above-identified commercially available ion chromatograph. The column 36 may include a suppression column, not shown, depending on the eluent being used. The separation column 36 is connected to a valve 38 which is operably connected to a second valve 40 for simultaneous operation therewith to move from respective positions a to positions b. The valves 38, 40 may be constructed as an integral valve unit having the flow directing capabilities indicated by the schematic diagram. The valve 38 is connected to an ion detection unit 42 which may be of the relative electrical conductivity measurement type and which may be appropriately configured depending on the particular type of fluid being sampled. The detection unit 42 may also be part of the above-mentioned chromatograph.

As illustrated in FIG. 1, the valve 40 is in communication with the valve 24 by way of a conduit 44 and the valves 38 and 40 are in communication with each other by way of a tee fitting or conduit 46 which is connected to fluid mixing means 48. The mixing means 48 may be a conduit coil having a plurality of turbulating devices disposed therein such as a series of glass beads or other means which will result in thorough mixing of fluid entering the mixing means 48 by way of the valves 38 and 40. The mixing conduit 48 is connected to the valve 30 by way of a conduit 50. The valves 24 and 26 are also interconnected by a conduit 52 having a reservoir portion of predetermined volume and the valves 28 and 30, making up a cooperable valve unit, are also interconnected by a conduit 54 having a reservoir portion of predetermined volume. The reservoir conduits 52 and 54 may be conduits of specified length and cross sectional flow area interconnecting their respective ports of the valves 24 and 26 and the valves 28 and 30.

The valve 26 is operable to place the reservoir conduit 52 in communication with a source of fluid to be sampled by way of a conduit 58 and a pump 60. The pump 60 is adapted to have a programmable controller 62 whereby the displacement and flow rate of the pump may be relatively precisely controlled during operation of the apparatus 22. The pump 60 may, in fact, be a stepper motor driven syringe such as model 401 Dilutor manufactured by Gilson Medical Electronics Inc., Middletown, Wisc. The syringe controller may be of a type 212B also manufactured by Gilsom Medical Electronics Inc. Fluid samples are supplied to the pump 60 from a source 64 which may comprise an automatic fluid sampling device such as a model 32297 manufactured by Dionex Corporation. The controller 62 and the valves 24, 26, 28, 30 and 38, 40 may be controlled by a central processing unit 66 such as a Series 9000 computer manufactured by Hewlett Packard Company. A suitable interface 68 is adapted to convert computer command signals to appropriate signals for operating the controller 62 and the respective valves connected to the interface. Signals indicating the conductivity of the fluid passing through the detection unit 42, or other means of detection, depending on the type of detection unit used, are input to the computer 66 through the interface 68 and converted to readable diagrams which may be displayed on a printer 70 and having the format illustrated in FIGS. 2 through 4.

The operation of the apparatus 22 and the methods of the present invention may be carried out in one of several ways as will now be described. If it desired to measure an undiluted sample from the source 64, the apparatus is first conditioned with the valves 24, 26, 28, 30, 38 and 40 in their respective positions a as illustrated in FIG. 1. The pump 32 continuously pump eluent through conduit 33 to the separation column 36 and the valve 38 and through the detection unit 42 to waste discharge by way of conduit 43. The conduits 58, 52, the valves 24 and 26, the conduit 44 and the valve 40 are suitably purged by fluid to be sampled as the pump 60 is operated to fill the reservoir conduit 52 with the sample to be analyzed. Fluid to be sampled is flushed through the portions of the system described above and discharged from the valve 40 by way of a waste conduit 41.

When it is desired to analyze a sample in the reservoir conduit 52, displacement of fluid through the conduit 58 by the pump 60 is terminated and the valves 24 and 26 are shifted to their positions b whereby a sample in the conduit 52 is carried by the eluent in conduit 33 through the separation column 36 and the detection unit 42 for recording a chromatogram in accordance with conventional operation of the above-mentioned commercial chromatograph. During measurement in this so-called standard mode, the valves 38 and 40 remain in their positions a. The valves 28 and 30 remain in their positions a during the injection of the sample from the reservoir conduit 52.

The apparatus 22 may also be utilized to conduct a so-called "online" chromatogram of a diluted sample of fluid from the source 64. The apparatus 22 is conditioned for measurement of a diluted sample of fluid by placing the valves 24 and 26 in their positions a, the valves 28 and 30 in their positions a and the valves 38 and 40 also in their positions a while the pumps 32 and 60 are operated to purge the flow paths adapted to receive the respective fluids with the valves in the above-mentioned positions. The pumps 32 and 60 may be adjusted as to their flow rates to provide the required dilution of the fluid from the source 64 with the eluent from the source 34 which is now used also as a diluent. When the flow rates of the pumps 32 and 60 have been adjusted the valves 38 and 40 are shifted simultaneously to their positions b so that a fluid mixture is conducted through the tee 46 and the mixing conduit 48 and to the reservoir conduit 54. After a predetermined time period which provides for complete filling of a thoroughly mixed or diluted solution in the reservoir conduit 54 between valves 28 and 30, the valves 38 and 40 are returned to their positions a. If necessary, the flow rate of pump 32 is then adjusted to the eluent flow rate normally used for the displacement or injection of the fluid sample into the separation column and the detection unit. When flow adjustment is completed and the separation column 36 and detection unit 42 suitably flushed, the valves 28 and 30 are shifted simultaneously to their positions b whereupon eluent from the pump 32 displaces the diluted fluid sample in the reservoir conduit 54 for injection into the separation column 36 and the detection unit 42. Analysis of the diluted fluid sample is then carried out in a conventional manner and the diluted sample recorded to yield a chromatogram similar to that of FIG. 3, for example.

An improved method of determining the composition of major and minor components of a fluid sample may be advantageously carried out using the apparatus 22 in yet another mode of operation. With the valves 24, 26, 28, 30, 38 and 40 in their positions a, the pumps 32 and 60 are operated to flush the system flow paths associated with the mentioned valve positions. The combination of the valves 24 and 26 and the combination of the valves 28 and 30 will be shifted from their respective positions a to their respective positions b in a predetermined sequence to provide a chromatogram as indicated in FIG. 4. For example, if a highly concentrated component, as indicated by the peak 80 in FIG. 4, is one which is given up early by the separation column 36 and detected by the detection unit 42 and is followed by detection of the lesser concentrated components indicated by the peaks 82, 84, 86 and 88, then the diluted sample can be passed through the separation column and the detection unit at a predetermined time delay with respect to the injection of the undiluted fluid sample so that a measurable peak for the component having the highest concentration, as indicated by the peak 90, may be superimposed on the chromatogram for the sample which was run in the undiluted mode whereby a complete chromatogram or record of the concentrations of the diluted and undiluted samples are provided simultaneously.

On the other hand, if the component of the fluid sample having the highest concentration is detected late in the detection phase of determining the components of the fluid sample, the diluted sample may be injected to and through the separation column 36 and the detection unit 42 before the injection of the undiluted sample. The timing of the injection steps may, of course, be selectively controlled by the central processing unit 66. By way of example, essentially simultaneous determination of the major and minor components of a fluid sample may be carried out in accordance with the following procedure. Assuming that the basic composition of a sample was known, and therefore the presence of either early or late separated ions, the central processing unit 66 would be instructed to effect control of shifting of the valve groups 24, 26 and 28, 30 in a predetermined sequence. Prior to operation of the apparatus to perform the simultaneous chromatographic analysis all of the valves would be in their positions a and the pumps 32 and 60 instructed to flush the associated fluid flow paths, accordingly.

Assuming that the diluted sample was to be injected after injection of the undiluted sample, the valves 24 and 26 would be shifted to position b at a predetermined time when a sample had filled and thoroughly flushed the reservoir conduit 52 whereby this sample would be injected through displacement by the eluent through the valves 28 and 30, still in their position a, the separation column 36, the valve 38 in its position a, and the detection unit 42. Subsequent to injection of the undiluted sample, the valves 24 and 26 would be shifted back to position a and the valves 38 and 40 shifted to position b to commence preparation of the diluted samples by mixing an undiluted quantity of the fluid to be measured with the eluent (now acting as a diluent) and loading of the thoroughly mixed and diluted sample into the reservoir conduit 54.

After a predetermined time when it is assured that a thoroughly mixed diluted sample is in the reservoir conduit 54, the valves 28 and 30 are shifted to position b while the valves 38 and 40 are shifted back to position a and the diluted sample is injected through the separation column 36 and the detection unit 42. As mentioned previously, the timing of injection of a diluted fluid sample is controlled such that the most concentrated ion is recorded to provide a chromatogram of the type illustrated in FIG. 4 wherein the diluted sample shows the concentration of the most highly concentrated ion within the scale of the chromatogram. The chromatogram would be appropriately noted that a conversion factor should be applied to the peak 90 with respect to the scale of the ordinate in FIG. 4.

After analysis of an undiluted and a diluted sample is carried out all of the valves are returned to their positions a in preparation for analysis of another sample by placing a sample source in flow communication with the pump 60. Repeated analysis of various samples may, of course, be substantially automated by control of the valves as well as the pumps 32 and 60 by the central processing unit. The source 64 may be an automatic sampling unit for placing various fluid quantities in communication with the pump 60, selected at will. Moreover, the apparatus illustrated in FIG. 1 may be modified to place the detection unit 42 between the valve 38 and the separation column 36 which does not affect the operation of the apparatus as described.

By providing and operating an apparatus, such as the apparatus 22, according to the method of the present invention, a substantial savings in time is realized for analyzing the components of a fluid sample wherein a relatively high concentration of a particular component is expected and would adversely affect the operation of the system without suitable sample dilution. Moreover, a single chromatogram may be produced in accordance with the method of the present invention which provides a record of all of the components of the fluid in question on a single recording during a process which provides considerable time savings.

EXAMPLE I

A chromatogram of a sample of subterranean formation water was obtained having the characteristics indicated generally in FIGS. 2, 3 and 4. A chromatogram according to FIG. 2 was obtained from an undiluted sample to determine the concentration of the following ions: bromide (peak 12), nitrate (peak 14), phosphate (peak 16) and sulphate (peak 18). It was clear from the chromatogram of FIG. 2 that the chloride ion (peak 10) was not measurable in an undiluted sample. Accordingly, a second chromatogram was obtained on a sample of the same fluid diluted 1:500 with deionized water to determine the concentration of chloride as indicated by peak 20 in FIG. 3. A sample of the same fluid was then run to obtain an online chromatogram of the diluted and undiluted samples as indicated by FIG. 4 where the concentration of chloride in the diluted sample is indicated by the peak 90. By changing the timing of the shifting of the valve groups 24, 26 and 28, 30 it is, of course, possible to move the chloride peak 90 to any location desirable on the chromatogram. In the online analysis of both the diluted and undiluted sample, the eluent had a composition of 2.8 mN $Na_2 CO_3$/0.8 L mN $NaHCO_3$. A micromembrane suppressor column comprising a model 038019 manufactured by Dionex Corporation was interposed in the flow path between the separation column and the detection unit.

Clearly, from the foregoing, when the eluent can also be used as the diluent an additional time saving is realized. In those instances when the eluent and diluent must be separate compositions the apparatus 22 may be modified to provide a separate source of diluent which may be placed in communication with the mixing tee 46 by way of a separate valve in place of or interposed between the valve 40 and the mixing tee.

Although certain preferred embodiments of the present invention have been described in some detail herein, those skilled in the art will recognize that the analysis of diluted an undiluted fluid samples in accordance with the invention may be carried out on apparatus other than an ion chromatograph including one of the type identified herein. Moreover, various other substitutions and modifications may be made to the apparatus and the method described without departing from the scope and spirit of the invention as recited in the appended claims.

What is claimed is:

1. A method for the simultaneous analysis of diluted and undiluted fluid samples to determine the concentration of one or more ions in said fluid samples, respectively, comprising the steps of:
   providing analysis means including an ion detection unit, ion separation means adapted to be in communication with said detection unit, first pump means for supplying an eluent for displacing a fluid sample to be measured through said separation means and said detection unit, second pump means for supplying an undiluted sample of fluid to be analyzed to said separation means and said detection unit, first reservoir means for holding a predetermined quantity of an undiluted sample of said fluid, second reservoir means for holding a predetermined quantity of a diluted sample of said fluid and valve means for selectively placing said reservoir means, respectively, in flow communication with said separation means and said first pump means;
   filling said first reservoir means with an undiluted fluid sample;
   mixing a quantity of undiluted fluid with a diluent to form a diluted sample of fluid and filling said second reservoir means with said diluted sample of fluid;
   selectively operating said valve means to displace one of said samples of fluid through said separation means and said detection unit and followed by the other sample of fluid to be displaced through said separation means and said detection unit in timed relationship such that the concentration of the most concentrated component of said fluid sample and said least concentrated component of said fluid sample may be detected within a predetermined time period to provide an analysis of the components of said fluid sample by said detection unit.

2. The method set forth in claim 1 wherein:
   said eluent is mixed with said fluid to form said diluted sample.

3. A method or providing an ion chromatogram of a particular fluid using an ion chromatograph comprising an ion separation column and a conductivity testing unit adapted to be in flow communication with each other for receiving a fluid sample in which ions are detained in said separation column and subsequently released for conductivity measurement in said conductivity testing unit, a source of fluid to be tested and controllable fluid pump means in communication with said source of fluid, a source of eluent, eluent pump means for displacing said fluid sample through said separation column and said conductivity testing unit with said eluent, reservoir means for storing a diluted sample and an undiluted sample of said fluid, respectively, and valve means for placing said source of eluent in flow communication with said reservoir means, respectively, for displacing fluid samples from said reservoir means to and through said separation column and said conductivity testing unit, said method comprising the steps of:
   pumping an undiluted sample of fluid to said reservoir means, respectively; and
   operating said valve means to displace one of said fluid samples with said eluent to and through said separation column and said conductivity testing unit, then interrupting the flow of said one fluid sample and displacing the other fluid sample through said separation column and said conductivity testing unit with said eluent in such a way that the most concentrated ion in said fluid is measured by said conductivity testing unit in a diluted sample before the least concentrated ion is measured by said conductivity testing unit.

4. The method set forth in claim 3, wherein:
   said diluted fluid sample is prepared by mixing an undiluted quantity of fluid with a quantity of eluent and stored in one of said reservoir means prior to measurement of the concentration of ions in said diluted sample.

5. The method set forth in claim 4, wherein:
   said apparatus includes means for mixing said fluid with said eluent to prepare said diluted fluid sample, and the steps of preparing said diluted fluid sample and displacing said diluted fluid sample to one of said reservoir means are carried out simultaneously with conducting an undiluted fluid sample to the other of said reservoir means.

* * * * *